United States Patent
Lum et al.

(10) Patent No.: US 7,576,186 B2
(45) Date of Patent: Aug. 18, 2009

(54) COMPOSITIONS AND METHODS FOR STEM CELL DELIVERY

(75) Inventors: Lawrence G. Lum, Coventry, RI (US); Randall J. Lee, Hillsborough, CA (US)

(73) Assignees: Roger Williams Hospital, Providence, RI (US); TransTarget, Inc., Burlingame, CA (US)

( * ) Notice: Subject to any disclaimer, the term of this patent is extended or adjusted under 35 U.S.C. 154(b) by 0 days.

(21) Appl. No.: 10/553,853

(22) PCT Filed: Apr. 23, 2003

(86) PCT No.: PCT/US03/12679
§ 371 (c)(1), (2), (4) Date: Oct. 20, 2006

(87) PCT Pub. No.: WO03/091398
PCT Pub. Date: Nov. 6, 2003

(65) Prior Publication Data
US 2007/0110733 A1 May 17, 2007

Related U.S. Application Data

(60) Provisional application No. 60/374,929, filed on Apr. 23, 2002.

(51) Int. Cl.
*C07K 16/00* (2006.01)

(52) U.S. Cl. ................................... 530/387.3

(58) Field of Classification Search .................. None
See application file for complete search history.

(56) References Cited

U.S. PATENT DOCUMENTS

| | | | |
|---|---|---|---|
| 5,762,930 A | 6/1998 | Fanger et al. | |
| 6,096,311 A | 8/2000 | Fanger et al. | |
| 7,282,222 B2 * | 10/2007 | Phillips | 424/577 |
| 2002/0041847 A1 * | 4/2002 | Goldenberg | 424/1.49 |
| 2006/0018897 A1 * | 1/2006 | Lee et al. | 424/130.1 |

FOREIGN PATENT DOCUMENTS

EP 0 294 703 12/1988

OTHER PUBLICATIONS

Sen et al., J of Hematology and Stem Research, 2001, 247-260.*
PCT International Search Report issued Nov. 14, 2003 in connection with PCT International Application No. PCT/US2003/012679, filed Apr. 23, 2003, PCT Publication No. WO/2003/091398 A3, published Nov. 6, 2003, on behalf of Roger Williams Hospital et al.
Communication Pursuant to Article 157(2)(a) EPC including Supplementary European Search Report issued Feb. 15, 2007 in connection with European Patent Application No. EP 03 73 1044, filed Apr. 23, 2003 on behalf of Roger Williams Hospital et al.
European Application No. 88 108 793.6, filed on Jun. 6, 1988, European Publication No. 0 294 703, published Dec. 14, 1988, on behalf of Dana-Farber Cancer Institute, Inc.
Almeida-Porada, G. et al. (1999) "Transplantation of Human Neuronal Stem Cells into Fetal Sheep Give Rise to Hematopoietic Cells In Vivo," *Blood* 94: 129a (abstract #567).
Bjornson, C. et al. (1999) "Turning Brain Into Blood: A Hematopoietic Fate Adopted by Adult Neural Stem Cells In Vivo," *Science* 283:534-537.
Ferrari, G. et al. (1998) "Muscle Regeneration by Bone Marrow-Derived Myogenic Progenitors," *Science* 279:1528-1530.
Gussoni, E. et al. (1999) "Dystrophin Expression in the *mdx* Mouse Restored by Stem Cell Transplantation," *Nature* 401:390-394 (Exhibit 7).
Jackson, K. A. et al. (1999) "Hematopoietic Potential of Stem Cells Isolated from Murine Skeletal Muscle," *Proc. Natl. Acad. Sci. U.S.A.* 96:14482-14486 (Exhibit 8).
Kawada, H. et al. (2001) "Bone Marrow Origin of Hematopoietic Progenitors and Stem Cells in Murine Muscle," *Blood* 98:2008-2013 (Exhibit 9).
Krause, D. S. et al. (2001) "Multi-Organ, Multi-Lineage Engraftment by a Single Bone Marrow-Derived Stem Cell," *Cell* 105:369-377 (Exhibit 10).
Lagasse, E. et al. (2000) "Purified Hematopoietic Stem Cells can Differentiate into Hepatocytes in vivo," *Nat. Med.* 6:1229-1234 (Exhibit 11).
Lum, L. et al. (2001) "Activated T-Cell and Bispecific Antibody Immunotheraphy For High-Risk Breast Cancer," *Acta Haematol.* 105:130-136 (Exhibit 12).
Orlic, D. (2001) "Hematopoietic Cells Regenerate Infarcted Myocardium," *Exp. Hematol.* (Suppl) 29:4 (abstract #10) (Exhibit 13).
Orlic, D. et al. (2000) "Transplanted Hematopoietic Stem Cells Repair Myocardial Infarcts," *Blood* 96:221a (abstract #943).
Petersen, B. E. et al. (1999) "Bone Marrow as a Potential Source of Hepatic Oval Cells", *Science* 284:1168-1170.
Riedle, S. et al. (1998) "In Vivo Activation and Expansion of T Cells By a Bi-Specific Antibody Abolishes Metastasis Formation of Human Melanoma Cells in SCID Mice," *Int. J. Cancer* 75:908-918.
Theise, N. D. et al. (2000) "Derivation of Hepatocytes from Bone Marrow Cells in Mice after Radiation-induced Myeloblation," *Hepatology* 31:235-240.
Valtz, N. L. et al. (1991) "An Embryonic Origin for Medulloblastoma," *New Biologist* 3:364-371.
Wakitani, S. et al. (1995) "Myogenic Cells Derived from Rat Bone Marrow Mesenchymal Stem Cells Exposed to 5-Azacytidine," *Muscle Nerve* 18:1417-1426.
Jackson, K.A. et al. (1999) "Hematopoietic Potential of Stem Cells Isolated from Murine Skeletal Muscle," *Proc. Natl. Acad. Sci. U.S.A.* 96:14482-14486.
Krause, D.S. et al. (2001) "Multi-Organ, Multi-Lineage Engraftment by a Single Bone Marrow-Derived Stem Cell," *Cell* 105:369-377.
Petersen, B.E. et al. (1999) "Bone Marrow as a Potential Source of Hepatic Oval Cells", *Science* 284:1168-1170.
Theise, N.D. et al. (2000) "Derivation of Hepatocytes from Bone Marrow Cells in Mice after Radiation-induced Myeloblation," *Hepatology* 31:235-240.
Valtz, N.L. et al. (1991) "An Embryonic Origin for Medulloblastoma," *New Biologist* 3:364-371.

* cited by examiner

*Primary Examiner*—Michail A Belyavskyi
(74) *Attorney, Agent, or Firm*—Townsend and Townsend and Crew LLP

(57) ABSTRACT

This invention provides compositions of matter, articles of manufacture and methods for delivering and/or affixing a stem cell to a target tissue. This invention also provides related nucleic acids, vectors, cell, methods of production, and kits.

2 Claims, No Drawings

COMPOSITIONS AND METHODS FOR STEM CELL DELIVERY

This application is a §371 national stage of PCT International Application No. PCT/US2003/012679, filed Apr. 23, 2003, claiming priority of U.S. Provisional Application No. 60/374,929, filed Apr. 23, 2002, the contents of all of which are hereby incorporated by reference.

Throughout this application, various references are cited. Disclosure of these references in their entirety is hereby incorporated by reference into this application to more fully describe the state of the art to-which this invention pertains.

BACKGROUND OF THE INVENTION

The era of plasticity began with the publication of a manuscript entitled "Turning brain into blood: a hematopoietic fate adopted by adult neural stem cells in vivo" by Bjornson and colleagues (1). They pursued a hypothesis based on observations made by Valtz et al. who showed the ability of a single neuroectodermal cell (from rat cerebellar cell line ST15A) to form neuronal, glial, and muscle cells (2). A deluge of plasticity papers has since followed.

Initially, there were reports of cells from muscle giving rise to hematopoiesis (3) and then a variety of reports of marrow-derived cells giving rise to muscle (4-6), hepatocytes (7-9) and cardiac myocytes (10, 11). This suggested that hierarchical plasticity is the rule and that the local microenvironment determines the choice of differentiation pathways.

While most of these studies have been done with whole cell populations, several experimental designs have used highly purified hematopoietic marrow stem cells, showing that hepatocytes and myocardial myocytes could arise from these cells. However, even in this instance, the results did not address the question of whether the repopulating cells were cells with both hematopoietic and nonhematopoietic potential or whether there coexisted separate lineage-defined stem cells in the purified population experimentally obtained. Work from Verfaille and colleagues provides support for the concept of multiple stem cell types residing in the marrow. In their in vitro studies, they found a class of stem cells which can give rise to neural, mesenchymal, muscle and fat cells, but not to hematopoietic lineages. The question of origin can only be answered with clonal population studies. One such study, using limiting dilution techniques, has been reported and indicates clonal origin of many nonhematopoietic cell types from purified marrow hematopoietic stem cells (12).

Another unresolved issue is whether the hematopoietic potential demonstrated in nonhematopoietic tissue arose from nonhematopoietic tissue stem cells or hematopoietic stem cells, which coexisted in the nonhematopoietic tissue. The initial reports of muscle cells generating hematopoiesis implied that muscle stem cells were responsible. However, recent work from Kawada and Ogawa (13) indicates that these initial reports simply demonstrate the existence of hematopoietic stem cells, which are known to circulate in the blood, within the muscle tissue. That study demonstrates that following reconstitution of irradiated mice with genetically marked bone marrow cells, the cells from the muscle tissue that had reconstituted hematopoietic progeny were all of donor origin.

In vivo observations of stem cell plasticity have been extended to human cells. Almeida-Porada and coworkers (14), using a permissive, pre-immune fetal sheep engraftment model, have shown that non-purified fetal human brain cells ("neurosphere" cells) can give rise to hematopoietic, hepatic, renal and gut cells. These data clearly indicate that different tissues harbor cells with lineage potential for many other tissues, and that marrow is a particularly abundant source for these cells. They further indicate the overriding importance of specific microenvironments and their associated differentiation cues. Unfortunately, they do not as yet establish whether true hierarchical plasticity exists or whether multiple stem cells coexist in various tissues.

This model, of course, may hold for many other tissues, regardless of whether there are single or multiple stem cell types. When stem cells emigrate or are injected into a tissue, differentiation would be determined by the local environment. Thus, cardiac tissue might harbor, at least transiently, all stem cell types, but only cardiac-type stem cells would differentiate and make heart cells. Alternatively, one stem cell with open potential may be involved and its differentiation fate would then be determined by inductive signals delivered by the local environment.

There is another intriguing possibility, which is that the marrow could actually be the feeder tissue for all other local stem cell populations. In this scenario, marrow stem cells with general potential are continuously circulating and these circulating cells would be the source of local stem cells in the gut, skin, liver or brain. Thus, the marrow would be the ultimate source of all stem cells and would feed the tissue stem cells. This would still be consistent with there being one marrow stem cell with total plastic potential or many individual stem cells with specific lineage potentials.

Notwithstanding the mechanisms of stem cell biology being studied, there exists a need for technology permitting the delivery and affixing of stem cells to particular target tissues. At present, however, such technology has not been adequately developed.

SUMMARY OF THE INVENTION

This invention provides a first composition of matter for delivering and/or affixing a stem cell to a target tissue comprising a first moiety that specifically binds to the stem cell surface operably affixed to a second moiety that specifically binds to the surface of a cell in the tissue.

This invention also provides a nucleic acid encoding a polypeptide for delivering and/or affixing a stem cell to a target tissue, which polypeptide comprises a first moiety that specifically binds to the stem cell surface operably linked to a second moiety that specifically binds to the surface of a cell in the tissue.

This invention further provides an expression vector comprising the instant nucleic acid, and a host-vector system comprising a host cell transfected with the instant expression vector.

This invention further provides a method for producing a polypeptide useful for delivering and/or affixing a stem cell to a target tissue, which polypeptide comprises a first moiety that specifically binds to the stem cell surface operably linked to a second moiety that specifically binds to the surface of a cell in the tissue, which method comprises (a) culturing the instant host-vector system under conditions permitting the expression of the polypeptide, and (b) recovering the polypeptide so expressed.

This invention further provides an article of manufacture for delivering and/or affixing a stem cell to a target tissue via juxtaposition of the article to the target tissue, comprising a solid substrate having operably affixed thereto a composition of matter comprising a moiety that specifically binds to the stem cell surface.

This invention further provides three methods for delivering and/or affixing a stem cell to a subject's target tissue. The first method comprises contacting the tissue with the stem cell and a composition of matter comprising a first moiety that specifically binds to the stem cell surface operably linked to a second moiety that specifically binds to the surface of a cell in the tissue.

The second method comprises, in no particular order, the steps of (a) juxtaposing to the tissue an article of manufacture comprising a solid substrate having operably affixed thereto a composition of matter comprising a moiety that specifically binds to the stem cell surface, and (b) contacting the article with the stem cell.

The third method comprises juxtaposing to the tissue an article of manufacture comprising (a) a solid substrate having operably affixed thereto a composition of matter comprising a moiety that specifically binds to the stem cell surface, and (b) the stem cell bound to the article via the composition of matter affixed thereto.

This invention further provides a second composition of matter comprising (a) a stem cell to be delivered to and/or affixed to a target tissue, and (b) a composition of matter comprising a first moiety that specifically binds to the stem cell surface operably affixed to a second moiety that specifically binds to the surface of a cell in the tissue.

Finally, this invention provides two kits. The first kit comprises the first composition of matter and instructions for using same to deliver and/or affix a stem cell to a target tissue. The second kit comprises the instant article of manufacture and instructions for using same to deliver and/or affix a stem cell to a target tissue.

DETAILED DESCRIPTION OF THE INVENTION

Definitions

As used in this application, except as otherwise expressly provided herein, each of the following terms shall have the meaning set forth below.

"Administering" shall mean delivering in a manner which is effected or performed using any of the various methods and delivery systems known to those skilled in the art. Administering can be performed, for example, topically, intravenously, pericardially, orally, via implant, transmucosally, transdermally, intramuscularly, subcutaneously, intraperitoneally, intrathecally, intralymphatically, intralesionally, or epidurally. Administering can also be performed, for example, once, a plurality of times, and/or over one or more extended periods.

The term "antibody" includes, by way of example, both naturally occurring antibodies (e.g., IgG, IgM, IgE and IgA) and non-naturally occurring antibodies. The term "antibody" also includes polyclonal and monoclonal antibodies, and fragments thereof (e.g., antigen-binding portions). Furthermore, the term "antibody" includes chimeric antibodies, wholly synthetic antibodies, human and humanized antibodies, and fragments thereof.

"Host cells" include, but are not limited to, bacterial cells, yeast cells, fungal cells, insect cells, and mammalian cells. Mammalian cells can be transfected by methods well-known in the art such as calcium phosphate precipitation, electroporation and microinjection.

"Mammalian cell" shall mean any mammalian cell. Mammalian cells include, without limitation, cells which are normal, abnormal and transformed, and are exemplified by neurons, epithelial cells, muscle cells, blood cells, immune cells, stem cells, osteocytes, endothelial cells and blast cells.

The terms "nucleic acid", "polynucleotide" and "nucleic acid sequence" are used interchangeably herein, and each refers to a polymer of deoxyribonucleotides and/or ribonucleotides. The deoxyribonucleotides and ribonucleotides can be naturally occurring or synthetic analogues thereof.

"Pharmaceutically acceptable carriers" are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, chelating agents, inert gases, and the like.

The terms "polypeptide," "peptide" and "protein" are used interchangeably herein, and each means a polymer of amino acid residues. The amino acid residues can be naturally occurring or chemical analogues thereof. Polypeptides, peptides and proteins can also include modifications such as glycosylation, lipid attachment, sulfation, hydroxylation, and ADP-ribosylation.

"Specifically bind" shall mean that, with respect to the binding of a moiety to the surface of a cell, the moiety binds to that cell with a greater affinity than that with which it binds to the surface of most or all other cells. In the preferred embodiment, the moiety binds to that cell with a greater affinity than that with which it binds to the surface of all other cells.

"Stem cell" shall mean, without limitation, a cell that gives rise to a lineage of progeny cells. Examples of stem cells include CD34+ cells, CD45+ cells and embryonic stem cells. Surface adhesion molecules present on stem cells include, without limitation, IL-3 receptor, IL-6 receptor, IL-11 receptor, c-kit, VLA-4, VLA-5, L-selectin, PECAM-1 and Beta-1 integrin.

"Subject" shall mean any animal, such as a mammal or a bird, including, without limitation, a cow, a horse, a sheep, a pig, a dog, a cat, a rodent such as a mouse or rat, a turkey, a chicken and a primate. In the preferred embodiment, the subject is a human being.

"Target tissue" shall mean any biological tissue to which stem cell delivery and/or attachment is desired. Target tissue includes, without limitation, normal, damaged and diseased tissue.

"Vector" shall mean any nucleic acid vector known in the art. Such vectors include, but are not limited to, plasmid vectors, cosmid vectors, and bacteriophage vectors.

EMBODIMENTS OF THE INVENTION

This invention provides two compositions of matter. The first composition of matter is for delivering and/or affixing a stem cell to a target tissue which comprises a first moiety that specifically binds to the stem cell surface operably affixed to a second moiety that specifically binds to the surface of a cell in the tissue.

The second composition of matter is for delivering and/or affixing a stem cell to a target tissue which comprises (a) the stem cell and (b) a composition of matter which comprises a first moiety that specifically binds to the stem cell surface operably affixed to a second moiety that specifically binds to the surface of a cell in the tissue.

The first and second moieties can be of any type. In one embodiment of the instant compositions, the first and second moieties are antigen-binding portions of an antibody. Antigen-binding portions include, for example, Fab fragments.

In the instant compositions, the compositions can also comprise bi-specific antibodies. Moreover, these compositions can comprise a single polypeptide chain comprising the first and the second moieties. Further, the instant compositions can comprise a recombinantly produced polypeptide chain.

In the instant compositions, the first and second moieties can be affixed via any suitable means. In one embodiment, the first and second moieties are affixed via a chemical moiety. In another embodiment, the first and second moieties are affixed via a polypeptide moiety.

In the instant compositions, the stem cell can be any stem cell. In one embodiment, the stem cell is mammalian. Mammalian stem cells include, for example, stem cells from a cow, a horse, a sheep, a pig, a dog, a cat, a rodent and a primate. Preferably, the stem cell is human. Stem cells used in the instant invention also include, by way of example, $CD34^+$ cells and embryonic stem cells.

In the instant compositions, the target tissue can be any suitable target tissue including, for example, hepatic tissue, skin, epithelial tissue, connective tissue, articular tissue, bone tissue (including, for example, bone marrow and other hematopoietic cells), muscle tissue, neuronal tissue and cardiac tissue. In one embodiment, the target tissue is cardiac tissue. In another embodiment, the target tissue is skin. Cardiac tissue can be abnormal, and includes, without limitation, diseased myocardial tissue, damaged myocardial tissue, diseased valve tissue, damaged valve tissue, diseased cardiovascular tissue and damaged cardiovascular tissue. Likewise, skin can be abnormal and includes, without limitation, diseased and damaged skin. Moreover, biochemical features of the target tissue recognized by the target tissue-binding moieties of the instant compositions include, by way of example, myosin, cardiac troponin T, cardiac troponin I, actin, beta-myosin heavy chain, tropomyosin or any other feature to which such moieties can be directed.

In another embodiment of the instant compositions, the compositions further comprise a pharmaceutically acceptable carrier.

This invention also provides a nucleic acid which encodes a polypeptide that binds to a stem cell. In one embodiment, the nucleic acid is DNA or RNA, and in another embodiment, the nucleic acid is DNA.

The instant nucleic acid can be an expression vector. In one embodiment, the vector is selected from a plasmid, a cosmid, a bacteriophage and a eukaryotic virus. Eukaryotic viruses include, for example, adenoviruses and retrovirus.

This invention further provides a host-vector system comprising a host cell transfected with the instant expression vector.

This invention further provides a method for producing a polypeptide useful for delivering and/or affixing a stem cell to a target tissue, which polypeptide comprises a first moiety that specifically binds to the stem cell surface operably linked to a second moiety that specifically binds to the surface of a cell in the tissue, which method comprises (a) culturing the instant host-vector system under conditions permitting the expression of the polypeptide, and (b) recovering the polypeptide so expressed.

This invention further provides a first article of manufacture for delivering and/or affixing a stem cell to a target tissue via juxtaposition of the article to the target tissue, comprising a solid substrate having operably affixed thereto a composition of matter comprising a moiety that specifically binds to the stem cell surface.

In a preferred embodiment of this invention, the solid substrate is biodegradable. In another embodiment, the solid substrate comprises a polymer, such as teflon. In a further embodiment, the solid substrate comprises an agent selected from fibrin, vicryl, hyaluronic acid, polyethylene glycol, polylactic acid, polylactic-co-glycolic acid, collagen, thrombospondin, teflon, osteopontin and fibronectin.

The instant article can be in any suitable physical form including, for example, gauze, a bandage, suture, a stent, an implant or a polymeric matrix.

Preferably, the composition of matter affixed to the solid substrate further comprises a second moiety that specifically binds to the surface of a cell in the tissue. In one embodiment, the moiety is an antigen-binding portion of an antibody, such as a Fab fragment. In another embodiment, the composition comprises a bi-specific antibody. In a further embodiment, the composition comprises a single polypeptide chain comprising the first and the second moieties. In still a further embodiment, the composition comprises a recombinantly produced polypeptide chain.

In the instant article, the first and second moieties can be affixed by any suitable means, such as via a chemical moiety and via a polypeptide moiety.

In the instant article, the stem cell can be any stem cell. In one embodiment, the stem cell is mammalian. Mammalian stem cells include, for example, stem cells from a cow, a horse, a sheep, a pig, a dog, a cat, a rodent and a primate. In another embodiment, the stem cell is avian. Avian stem cells include, for example, turkey and chicken stem cells. Preferably, the stem cell is human.

Also in the instant article, the target tissue can be any suitable target tissue including, for example, hepatic tissue, skin, epithelial tissue, connective tissue, articular tissue, bone tissue, muscle tissue, neuronal tissue and cardiac tissue. In one embodiment, the target tissue is cardiac tissue.

This invention further provides a second article of manufacture intended for the affixation of stem cells to the article's surface, comprising a solid substrate having on its surface a moiety which is specifically bound by a composition of matter which also specifically binds to a stem cell.

The various embodiments of the first article of manufacture, such as the nature and physical form of substrate, are envisioned, as applicable, for the second article of manufacture.

This invention further provides three methods for delivering and/or affixing a stem cell to a subject's target tissue. The first method comprises contacting the tissue with the stem cell and a composition of matter comprising a first moiety that specifically binds to the stem cell surface operably affixed to a second moiety that specifically binds to the surface of a cell in the tissue.

In one embodiment of the first method, the contacting is performed ex vivo. In another embodiment, the contacting is performed in vivo.

In another embodiment of the first method, the stem cell and composition of matter are first contacted with each other so as to permit the formation of a complex therebetween, and the resulting complex is contacted with the target tissue. The complex can be contacted with the target tissue via any suitable means, such as topical or intravenous administration.

In the first method, the first and second moieties can be of any type. In one embodiment, the first and second moieties are antigen-binding portions of an antibody. Antigen-binding portions include, for example, Fab fragments.

Also in the first method, the composition can comprise a bi-specific antibody. Moreover, this composition can comprise a single polypeptide chain comprising the first and the second moieties. Further, the composition can comprise a recombinantly produced polypeptide chain.

In the first method, the first and second moieties can be affixed via any suitable means. In one embodiment, the first and second moieties are affixed via a chemical moiety. In another embodiment, the first and second moieties are affixed via a polypeptide moiety.

The second method for delivering and/or affixing a stem cell to a subject's target tissue comprises, in no particular order, the steps of (a) juxtaposing to the tissue an article of manufacture comprising a solid substrate having operably affixed thereto a composition of matter comprising a moiety that specifically binds to the stem cell surface, and (b) contacting the article with the stem cell.

In one embodiment of the first method, the article is contacted with the stem cell via intravenous administration of the stem cell. In one embodiment of the second method, the article is contacted with the stem cell via topical administration of the stem cell.

The third method for delivering and/or affixing a stem cell to a subject's target tissue comprises juxtaposing to the tissue an article of manufacture comprising (a) a solid substrate having operably affixed thereto a composition of matter comprising a moiety that specifically binds to the stem cell surface, and (b) the stem cell bound to the article via the composition of matter affixed thereto.

In the instant methods, the article can be in any suitable physical form including, for example, gauze, a bandage, suture, a stent or a polymeric matrix.

Preferably in the instant methods, the composition of matter affixed to the solid substrate further comprises a second moiety that specifically binds to the surface of a cell in the tissue. In one embodiment, the moiety is an antigen-binding portion of an antibody, such as a Fab fragment. In another embodiment, the composition comprises a bi-specific antibody. In a further embodiment, the composition comprises a single polypeptide chain comprising a first and a second moiety that specifically bind to the stem cell surface and tissue cell surface, respectively. In still a further embodiment, the composition comprises a recombinantly produced polypeptide chain.

In the instant methods, the first and second moieties can be affixed by any suitable means, such as via a chemical moiety and via a polypeptide moiety.

The subject in the instant methods can be any subject. Likewise, the stem cell can be a stem cell from any subject. In one embodiment, the subject is a mammal. Mammals include, for example, a cow, a horse, a sheep, a pig, a dog, a cat, a rodent and a primate. In another embodiment, the subject is a bird. Birds include, for example, turkeys and chickens. Preferably, the subject is human, and the stem cell is human.

In the instant methods, the target tissue can be any suitable target tissue including, for example, hepatic tissue, skin, epithelial tissue, connective tissue, articular tissue, bone tissue, muscle tissue, neuronal tissue and cardiac tissue. In one embodiment, the target tissue is cardiac tissue.

Finally, this invention further provides kits for delivering and/or affixing a stem cell to a target tissue. The first kit comprises the first instant composition of matter and instructions for use. The second kit comprises the instant article of manufacture and instructions for use.

This invention will be better understood from the Examples that follow. However, one skilled in the art will readily appreciate that the specific methods and results discussed are merely illustrative of the invention as described more fully in the claims which follow thereafter.

EXAMPLES

Example 1

Examples of Therapeutic Indications for Stem Cell Therapy

Organ Failure States
  Cardiac disorders (e.g., myocardial infarction, valvular disease, hypertrophic/restrictive diseases, myocarditis and cardiomyopathy); kidney failure, acute and chronic; liver failure, acute and chronic; lung failure, acute and chronic; COPD and ARDS; and skin failure such as dermatological disorders, diabetic ulcers, burns, chemotherapy or radiation damage, and cancer-related skin damage.

Neurologic Disorders
  Alzheimer's and other degenerative disorders; structural damage to brain or spinal cord from stroke or trauma; peripheral neuropathy; and degenerative disorders (e.g., Amyotrophic Lateral Sclerosis (Lou Gehrig's disease) and Guillain-Barre syndrome).

Malignancies
  Primary bone marrow disorders (e.g., leukemia, myelodysplastic syndrome); and solid tumors.

Autoimmune Diseases
  Systemic lupus erythematosus, eczema, psoriasis, and ITP.

Genetic-based Diseases
  Sickle cell anemia, thalassemia, hemoglobinopathies, and hemophilia.

All Known Stem Cell Diseases
  Chronic myelogenous leukemia; most acute leukemias; polycythemia rubra vera, primary thrombocytosis; myelofibrosis with myeloid metaplasia, aplastic anemia; paroxysmal nocturnal hemglobinuria; most lymphomas and multiple myeloma; many chronic neutropenias; pure red cell aplasia and Fanconi's anemia; and cyclic neutropenias and Shwachman-Diamond syndrome.

Example 2

The Potential of Skin Stem Cells Arising from Bone Marrow

Introduction
  A number of tissue stem cell systems have been described. The hematopoietic system has perhaps been most extensively characterized. The hematopoietic stem cell has been felt to be a cell with extensive proliferative, renewal and differentiative potential for red cell, white cell and platelet lineages. In similar fashion, stem cells in intestinal crypts, hippocampal, subventricular zone, neural crest, and eye conjunctival have also been shown to produce major cell types in their respective organs. Less well-characterized stem cell systems have been reported for muscle and liver. Hair follicle bulge stem cells produce epithelial cells, cells for the outer root sheath and matrix as well as lipid-producing sebaceous glands. Epidermal skin stem cells have been partially characterized by cell surface markers, size and in vitro adhesion characteristics. Both label-retaining and transient amplifying populations have been described. Isolation of skin stem cells using cell size and Hoechst red/blue dye exclusion has recently been described. This technique is an adaptation of a well-characterized method for isolating hematopoietic stem cells. In a recent study, stem cells in skin dermis have also been described.

Recently, it has been appreciated that stem cells may show tremendous plasticity and that a stem cell from one tissue may commit to a different fate when located in a different tissue. There has followed a large number of reports showing that muscle and hepatic cells can make blood cells, that adipose cells can differentiate into chondrocytic, myogenic and osteogenic lineages and that marrow cells can produce a wide variety of cell types. Marrow has now been shown to be capable of producing, in vitro and in vivo, hepatic, renal, pulmonary, gastrointestinal, neural, chondrocyte, adipocyte, cardiac and skeletal muscle, as well as bone cells. Two particularly impressive studies have shown highly purified murine stem cells to be capable of producing hepatic cells or cardiac myocytes and of reversing disease manifestations in these organs. Recently, Ogawa and colleagues have published data indicating that the skeletal muscle stem cells, which were reported as having hematopoietic potential, may have originally derived from marrow.

These studies raise important questions as to the source of many, or possibly all tissue stem cells. One possibility is that the marrow could be such a source. Marrow stem cells are continuously present in the peripheral blood and it is now known that marrow cells appear to have the capacity for generating many other cell types when residing in a specific tissue. Marrow cells may continuously renew tissue stem cells through the lifespan of an animal. Renewal of resident stem cells may be required for maintenance of an organ and for repair of damage due to injury. This may be of particular importance in highly regenerative organs such as the liver or skin, which are tissues very familiar with injury due to toxic insult or wounding. It is believed that wounding is in fact a mechanism by which stem cells are recruited to skin.

The failure of chronic wounds to heal may be due in part to the loss or malfunction of resident skin stem cells. This notion does not require a great leap of faith, as recent studies (data not shown) have shown that cells derived from chronic wounds appear altered in their growth capacity and in their ability to respond to certain cytokines. Cultured dermal fibroblasts appear senescent, as shown by their decreased capacity to undergo population doubling and by other parameters. Lower extremities from patients with advanced arterial and/or venous disease are also noted to have decreased numbers of hair follicles, which are the predominant source of epidermal skin stem cells in that body location. This reduction of follicles would then represent a loss of resident stem cells in the vicinity of chronic wounds.

The ability to bring new young cells into the wound is generally thought to explain the effectiveness of bioengineered skin in treating chronic wounds. Recent work (data not shown) has shown that delivery of bone marrow stem cells to wounds reverses the failure of chronic wounds to heal and promotes rebuilding of the dermal structures.

Many of these new observations have come about because of the availability of specific markers to track cell populations and labeling techniques to identify the nature of donor cells in a transplanted mouse. For example, markers for repetitive sequences on the Y chromosome recently became available allowing for the tracking of male cells in female hosts, especially in strains which do not show HY immunoreactivity. Both Southern blot and fluorescent-in-situ-hybridization (FISH) were utilized in those experiments. The availability of transgenic mice with specific markers has allowed for rapid progress in this field. The most commonly used systems have been markers for green fluorescent protein or for expression of β-galactosidase. Rosa mice transgenic for β-galactosidase expression have been used in many studies, while a number of GFP-transgenics have also been used.

Results

In the past, it was shown that marrow cells were able to give rise to bone cells when infused at relatively high levels (over 80 million) into non-ablated host mice. Morphology and FISH on serial marrow sections were used. Here, the marrow sections were prepared in a unique fashion using anesthetized mice and low-pressure paraformaldehyde infusion through the descending aorta.

More recently, a model was evaluated for transplanting green-fluorescent protein (GFP)-positive transgenic marrow cells into hosts and evaluating immediate homing and eventual cell fate in the skin and other tissues. In these studies, GFP+ transgenic mice were used as donors and C57BL/6J mice (same sex) were used as hosts. Host mice were exposed to 400 cGy whole body irradiation and then infused with 25 million GFP+ marrow cells. In some experiments CFDA-SE, a cytoplasmic nonspecific fluorescent probe, was also used to label the marrow cells. Cohorts of mice were maintained for 3 months and peripheral blood chimerism was assessed at different intervals. A stable chimerism of between 70-80% was achieved.

Three months post-marrow cell infusion mice were divided into 3 groups. One group was not further treated. The other two groups received two excisional wounds (per mouse) on the back. These wounded groups differed in that one group was given G-CSF twice daily for 4 consecutive days before wounding and on the day of wounding (total 5 days). The time of excisional wounding was counted as day 0 for all groups. On day 2, the non-wounded group had a skin biopsy performed on the back and the two wounded groups had one of their excisional wounds harvested for analysis. On day 21, the non-wounded group had a skin biopsy performed on the back and the two wounded groups had their remaining excisional wounds harvested for analysis. The tissues were evaluated for the presence of donor cells and for the phenotype of the donor cells.

There were several GFP+ cells in the dermis of the transplanted unwounded mice at both time points. This finding supports the notion that there is constant trafficking of bone marrow cells to the dermis. The spindle cell and round morphologies of these cells could indicate that these cells may be inflammatory in nature. However, the H&E stained companion sections did not reveal a significant inflammatory infiltrate. Rather, these cells appear to have a fibroblast or tissue macrophage like morphology. The number of GFP+ dermal cells in non-wounded transplanted mice was slightly higher than that in sections prepared from the skin of donor GFP+ mice. This finding might be a secondary effect of the radiation to which the transplanted mice were exposed. The effect of radiation could have been to locally reduce the number of resident progenitor cells. This may have created "room" for the bone marrow cells to repopulate the area.

In the wounded mice at day 2, there was a significant inflammatory infiltrate in both groups. In the G-CSF-treated group, the inflammatory infiltrate was much greater than in the non-G-CSF-treated group. The amount of GFP present in the wound due to the infiltrate and ruptured inflammatory cells obliterated the wound field with fluorescence in many cases. Interpretation of these sections for engraftment of cells was difficult in both wounded groups due to the high level of signal present. At day 21, the amount of inflammation in the wounded groups was mostly resolved. There did not seem to be a significant difference in the number of GFP+ cells in both wounded groups. Several GFP+ mature (and immature) blood vessels were noted in the dermis of both wounded groups. There were GFP+ cells noted in the striated muscle of the dermis, hair follicle, sebaceous glands and epidermis in both wounded groups. However, there seemed to be more GFP+ cells in the epidermis, hair follicles and sebaceous glands of the G-CSF-treated mice. Hair follicle, sebaceous gland and epidermal GFP+ cells were also shown to double label for keratin and GFP antibodies. These findings strongly support the idea that bone marrow may supply needed stem and/or progenitor cells to wounded cutaneous tissues.

Recently, chronic ulcers of greater than one-year duration were treated with autologous bone marrow derived cells. The patients selected had failed a number of sophisticated wound care treatments in an advanced wound care clinic. These prior treatments included autologous skin grafting and grafting with bioengineered skin. Biopsies obtained from these patients indicate that bone marrow cells engrafted into the wounds. To date, all patients treated with bone marrow cells are currently healed. As described above, it is well known that chronic wounds have an altered local environment with evidence of cell senescence and depletion of resident stem and/or progenitor cells. The instant work illustrates the significance of bone marrow in delivering stem and/or progenitor cells to wounds.

Example 3

Cell-Cycle Related Stem Cell Homing and Transdifferentiation

Introduction

Recent studies have indicated that marrow-derived stem cells have the capacity to home to and differentiate in nonhematopoietic tissues producing cells with nonhematopoietic lineages typical of that tissue, i.e., so-called transdifferentiation. In several studies, highly purified murine marrow stem cells were shown to repopulate diseased or injured hepatic and cardiac tissue, respectively, and were also shown to restore or improve function in these tissues. Thus, marrow stem cells evidence a remarkable plasticity with regard to making nonhematopoietic cells.

Others have studied a different type of marrow stem cell plasticity; that of cell cycle-related shifts in engraftment or differentiation phenotype of the stem cell. These studies suggested that when purified marrow stems are induced to transit cell cycle, they reversibly alter their adhesion protein profile that in turn effects homing. This homing then determines the results of engraftment in marrow.

Data

The above-described sequence of events was demonstrated when marrow was cultured with interleukin (IL)-3, IL-6, IL-11 and steel factor. Marrow cells were studied in standard static tissue culture conditions and in simulated microgravity using NASA-supplied rotating tissue culture vessels. These studies investigated both the impact of cycle progression induced by the cytokine cocktail IL-3, IL-6, IL-11 and steel factor or alternatively by thrombopoietin (TPO), FLT-3 ligand (FLT-3L) and steel factor on marrow cell engraftment and differentiation.

The results of these studies were as follows. (1) Growth under microgravity conditions appears to favor support of relatively differentiated cells. (2) Shifts of engraftment phenotype were seen with cytokine induced cell cycle transit under normal and microgravity conditions. (3) These engraftment phenotype shifts were reversible and in each case appeared tied to cell cycle. (4) Shifts in the differentiation phenotype were seen at points in cell cycle which differed from the shifts in the engraftment phenotype and which were also reversible. These latter observations are particularly important, in that they suggest the presence of differentiation "hotspots" at different points in the cell cycle. At certain points in the cell cycle, the purified cells (Lineage$^{negative\ (-)}$ Rhodamine (Rho) $^{low}$Hoechst (Ho) 33342$^{low}$) present the phenotype of a primitive engraftable stem cell while at other times the phenotype is that of a progenitor. This further suggests that there is no stem cell/progenitor hierarchy but rather a fluctuating continuum with continual and reversible changes in phenotype tied to the phase of the cell cycle.

Example 4

Bispecific Antibody Targeting of Stem Cells to Nonhematopoietic Tissues

Background and Results

Bispecific antibodies can be constructed by genetic engineering or chemical conjugation techniques. In recent studies, bispecific antibodies that link CD3 and HER2/neu were chemically conjugated which selectively bind T cells to HER2/neu-expressing tumor cells. It was shown that this binding results in significantly increased cytotoxic functions of T cells to breast cancer cells. Further work on molecular engineering of bispecific antibodies has shown that T cells armed with the recombinant protein containing only the scFv portions of two antibodies can specifically target and kill the tumor cells.

Recent studies indicate that marrow stem cells can give rise to a variety of cell types in different tissues and rapidly correct tissue dysfunction in vivo, and suggest that targeting of marrow stem cells to particular tissues could increase the efficiency of marrow-derived transdifferentiation in these tissues.

Project 1

The purpose of this project is to produce a bispecific monoclonal antibody (BsAb), anti-VCAM-1×anti-c-Kit (named VK-Bi), that will target marrow stem cells to skin. Bi-specific antibodies are created which link primitive murine lymphohematopoietic stem cells (Lin$^-$Rho$^{low}$Ho$^{low}$, Lin-Sca-1+, or Lin-Hoechst side population) to skin cells expressing the following injury ligands; VCAM-1, ICAM-1, P-selectin, IL-8 or P63. C-kit has been selected for the stem cell epitope because in recent studies, it was shown to be universally present on Lin$^-$Rho$^{low}$Ho$^{low}$ and Ho$^{low}$ and Lin-Sca+ murine marrow hematopoietic stem cells and because it has been used by a number of investigators to isolate homing and engrafting stem cells, i.e., binding of antibody to c-kit does not appear to interfere with stem cell homing and engraftment. Thus, the first bispecific antibody that is prepared, characterized and validated as a reagent is a heteroconjugate that binds on one end to c-kit and the other end to VCAM-1.

These two antibodies are conjugated through two reagents, the Traut and SMCC. The procedure of BsAb production has been well established. This heteroconjugation reaction includes two steps. (1) Anti-c-Kit is cross-linked with 10-fold molar excess of Traut reagent (2-iminothiolane HCL, Pierce)

and (2) anti-VCAM-1 with 4-fold molar excess of SMCC (sulphosuccinimidyl 4-(N-maleimidomethyl) cyclohexane-1-carboxylate, Pierce). The Traut Buffer contains 50 mM NaCl, 1 mM EDTA, pH 8.0 and the SMCC buffer, 0.1 M sodium phosphate, 0.15 M NaCl at pH 7.2. The cross-linking reaction takes place at room temperature for one hour. The cross-linked antibody is then purified on a PD-10 column (Pharmacia, Uppsala, Sweden) in PBS to remove unbound cross-linker. In the second step, the cross-linked antibodies are mixed immediately at an equal molar ratio and conjugated at 4° C. overnight on a shaker. Control bispecific antibodies are also created to evaluate the specificity of binding. Here, anti-c-kit and anti-irrelevant antibodies are used, e.g., anti-CD2.

Heteroconjugation products are confirmed by non-reducing SDS PAGE gels. The specificities of the bispecific antibody product is verified by studies of the ability of the bispecific antibody to bind stem cells to VCAM-1-expressing cells.

The unfractionated preparations of anti-c-Kit×anti-VCAM-1 contain monomers, dimers and multimers. Only 20-30% of heteroconjugation products are in dimer form. The total antibody mixture is assessed, including multimers, dimers and monomers. This mixture has been used effectively in the above-cited OKT3/HER2/neu bispecific antibody studies. The efficacy of dimer/multimer fractions purified by sizing chromatography is also assessed. This, of course, gives a more purified characterized reagent, but at the cost of significant loss of antibody (approximately 80-90% based on previous experience). This reagent should be sufficiently pure. The isolation of dimer free from multimer may be accomplished by use of ion exchange chromatography, but this would be at the cost of significant further loss of antibody. Perhaps the critical observation here is that the original preparation of bispecific antibody to OKT3/HER2/neu, which had multimers, dimers and monomers, effectively bound T cells to breast cancer cell line cells. Furthermore, in studies in which multimers, dimers and monomers were separated, binding activity was found in the dimer and multimer fractions.

Project 2

The purpose of this project is to evaluate the function of anti-c-Kit×anti-VCAM-1 in vitro using skin cell lines and biopsy skin tissues, and in vivo using the mouse model.

Specifically, this work is to determine whether a bispecific antibody binds to c-kit on purified Lin$^-$Rho$^{low}$Ho$^{low}$ or Lin-Sca+ or Lin-Hoechst side population marrow stem cells from male BALB/c or Rosa beta-galactosidase-positive mice, and mediates increased binding of the stem cells to epithelial cells expressing the injury ligands VCAM-1, ICAM-1, P63, E-selectin and IL-8.

Binding of the anti-c-kit×anti-VCAM-1 bispecific antibody to different skin cells and c-kit+ populations from different sources is evaluated. In in vitro studies, the bispecific antibodies are titrated in VCAM-1+ injured skin cells (not expressing c-kit) and to c-kit+ stem cells (not expressing VCAM-1). An irrelevant bispecific antibody is used as a control.

The in vivo homing of c-kit cells labeled with the non-specific fluorescent dye, CFDA-SE and with bound bispecific antibody to normal, biopsied or locally irradiated skin is monitored. These studies include homing, subsequent cell fate and determination of trans-differentiation.

Using established animal transplantation models, it is determined whether the bispecific antibody can augment the homing process of stem cells and enhance the differentiation in the target environment (the injured skin). In brief, beta-galactosidase-positive Rosa mice are used as marrow stem cell donors and C57BL/6J mice (same sex) are used as hosts. For the homing studies, the cytoplasmic dye CFDA-SE is used in tissue sections and fluorescent events enumerated.

In order to follow cell fate and possible "transdifferentiation", the intrinsic and invariant cell labels of either male DNA (the male to female BALB/c marrow transplant model) or beta-galactosidase (the Rosa to C57BL/6J marrow transplant model) are employed. This approach is necessary, because the CFDA-SE fluorescent label will be lost with continued proliferation. In these studies, double labeling studies are carried out. For male DNA, the presence of Y chromosome DNA is first determined using FISH for male sequence. These preparations are photographed and then restained for cell type-specific markers, mainly cytokeratins. These preparations are also photographed and the photos matched to determine double labeling. With the beta-galactosidase system, the sequence is reversed, first determining antibody staining and then the presence of beta-galactosidase by either x-gal staining or by anti-beta-galactosidase antibody staining.

These studies allow one to determine the capacity of murine marrow-derived stem cells with bound bispecific antibody to home to skin and then produce epithelial or other skin-associated cells. In these studies, homing and cell fate are also determined when stem cells are untreated or bound to an irrelevant bispecific antibody. Homing and cell fate are determined in normal mice or in mice which have been subjected to a skin wound or local skin irradiation (500-2000 cGy). These injuries will occur from one day to two weeks prior to cell infusion.

Example 5

Heart Injury Model

Project 1

A myocardial ligation model was established in mice, and has use for studying tissue injury repair. C57BL/6 animals underwent coronary artery ligation followed by injection of 40×10$^6$ bone marrow cells 24, 48 and 72 hours after injury. Animals were evaluated for transdifferentiation of GFP+ cells in heart sections at different time points after injury (up to one month). There was no evidence of GFP+ myocardial cells. In a different set of experiments, C57BL/6 animals were exposed to 500 cGy, followed by infusion of 25 million bone marrow cells from GFP transgenic mice. Two months later, their anterior descending coronary arteries were ligated, and after four days, the animals were injected with G-CSF to mobilize their bone marrow stem cells. The data show that in the mobilized animals, GFP+ myocardial cells can be identified (data not shown).

Project 2

Studies were conducted to see whether arming marrow cells with anti-c-kit×anti-VCAM1 bispecific antibody helps target marrow cells to an injured heart and to determine which c-kit+ cell population would be the appropriate population for cardiac homing. These studies compared the homing performance of Lin- cells and Lin-Sca+ cells armed with control and bispecific antibody.

In studies using Lin-Sca+ purified (250,000 cells injected) cells, there was no difference between the control and the bispecific antibody at 14 hours post-infusion. However, when using Lin-cells (450,000 cells injected), there was a significant increase in homing of marrow cells armed with anti-c-kit×anti-VCAM1 to the injured heart (Data not shown).

This illustrates that a partially purified population of marrow cells at a specific time post-infusion is enhanced in its targeting to the injured heart by arming with the marrow cell with an anti-c-kit×anti-VCAM1 bispecific antibody.

Project 3

Studies were conducted to determine whether purified Lin-Sca+ cells armed with anti-c-kit×anti-VCAM1 bispecific antibody would be retained after direct intramyocardial injections or would home to injured myocardium after intravenous injection in C57BL/6 mice following myocardial infarct surgery. Two mice were anesthesized with intraperitoneal injections of ketamine and xylazine, intubated and ventilated using a Harvard rodent respirator. A midline sternotomy was performed and a 7-0 Ticron coated suture was used to tie off and occlude the apical portion of the left anterior descending artery (LAD). The sternum and skin were closed with interrupted sutures. The mice were allowed to recover for 3 days. On the third day under isoflurane anesthesia, the mice had cut-downs performed on the right internal jugular (i.j.) vein. One mouse received 200,000 Lin-Sca+ purified cells armed with 500 ng of anti-c-kit×anti-VCAM-1/million cells and the second mouse received 200,000 unarmed Lin-Sca+ purified cells. Both the armed and unarmed Lin-Sca+ cells were labeled with CFDA-SE prior to i.j. injection.

Two other mice underwent the same infarct surgery as described above. One of the latter two mice received a direct intramyocardial injection of 200,000 CSFDA-SE labeled Lin-Sca+ cells armed with anti-c-kit×anti-VCAM1 and one received a direct intramyocardial injection of 200,000 CSFDA-SE labeled unarmed Lin-Sca+ cells. All four mice were sacrificed 6 days after their infarcts were performed and their hearts were excised, washed in saline, frozen in OCT and cryosectioned, mounted on Superfrost plus slides and viewed under fluorescence microscopy.

In the direct injection of armed Lin-Sca+ cells, the results show enhanced numbers of fluorescent cells at the site of injection in the infarct area over background auto-fluorescence at high magnification (data not shown). In the mouse that received armed CSFDA-SE labeled Lin-Sca+ cells via i.j. injection, there was clearly enhanced fluorescence with increased numbers of cells in the infarct zone that concentrated in the endocardial layers extending to epicardial layers (data not shown). In contrast, there was much less fluorescence in the infarct area in the mouse that received CSFDA-SE labeled unarmed Lin-Sca+ cells via i.j. injection.

This shows that armed Lin-Sca+ cells injected via the internal jugular vein can home to injured myocardium whereas unarmed Lin-Sca+ do not home to injured myocardium.

Project 4

Studies were conducted using human T cells armed with OKT3 (anti-human CD3)×anti-rat ICAM1 to confirm trafficking mediated by the targeting antibody. This was a proof of principle experiment that obviated the need for purifying and sorting large numbers of Lin-Sca+ purified stem cells from the bone marrow of thirty mice. Only 1-2 million Lin-Sca+ cells can be obtained from an all-day purification process. On the other hand, large numbers of homogenous anti-CD3 activated T cells grown in low dose IL-2 can be obtained and used as living "markers" for homing to target tissue that can be easily identified by staining to T cells using CY3 fluorochrome.

The purpose of this project is two-fold: (1) to find out whether arming cells with target-specific antibodies aids in the delivery of cells to the target organ via intravenous injection, and (2) to see whether arming cells with target-specific antibodies leads to higher cell retention after direct injection into the target organ.

Four groups of nude rats which had a 17-minute infarction followed by reperfusion 1 day prior to cell injection were used for this study. Infarction was caused by a transient ligation of their left anterior descending portion (LAD) of the left coronary artery. After 17 minutes, ligation was stopped to allow reperfusion. The animals were injected as follows: (1) i.j. injection of activated human T cells armed with mouse anti-rat ICAM1×mouse anti-human OKT3 bispecific antibody; (2) i.j. injection of activated human T cells armed with hamster anti-mouse ICAM1×mouse anti-human OKT3 bispecific antibody (control); (3) Direct myocardial injection of activated human T cells armed with mouse anti-rat ICAM1×mouse anti-human OKT3 bispecific antibody; and (4) Direct myocardial injection of activated human T cells armed with hamster anti-mouse ICAM1×mouse anti-human OKT3 bispecific antibody (control). The animals were then sacrificed 1 day later. Fresh frozen specimens of their ventricles were cryosectioned and then stained with immunofluorescent anti-mouse IgG antibodies conjugated to Cy3 to label armed cells with mouse-derived antibodies.

There was a marked difference between the two i.j. injection groups. The experimental group (activated human T cells armed with mouse anti-rat ICAM1×mouse anti-human OKT3 bispecific antibody) showed a significant increase in immunofluorescence and cellularity relative to the control group (data not shown). These findings show that arming cells with target-specific antibodies help markedly increase the i.j. delivery of the armed cells to the target organ. However, unlike i.j. injections, arming cells with target-specific antibodies does not lead to a higher retention of armed cells after direct myocardial injections (data not shown).

REFERENCES

1. Bjornson C. R., Rietze R. L., Reynolds B. A., Magli M. C., Vescovi A. L., Turning brain into blood: a hematopoietic fate adopted by adult neural stem cells in vivo. *Science* 1999, 283:534-537.
2. Valtz N. L., Hayes T. E., Norregaard T., Liu S. M., McKay R. D., An embryonic origin for medulloblastoma. *New Biologist* 1991, 3:364-71.
3. Jackson K. A., Mi T., Goodell M. A., Hematopoietic potential of stem cells isolated from murine skeletal muscle. *Proc Natl Acad Sci USA* 1999, 96:14482-14486.
4. Ferrari G., Cusella-DeAngelis G., Coletta M., et al., Muscle regeneration by bone marrow-derived myogenic progenitors. *Science* 1998, 279:1528-1530.
5. Gussoni E., Soneoka Y., Strickland C. D., et al., Dystrophin expression in the mdx mouse restored by stem cell transplantation. *Nature* 1999, 401:390-394.
6. Wakitani S., Saito T., Caplan A., Myogenic cells derived from rat bone marrow mesenchymal stem cells exposed to 5-azacytidine. *Muscle Nerve* 1995, 18:1417-1426.
7. Petersen B. E., Bowen W. C., Patrene K. D., et al., Bone marrow as a potential source of hepatic oval cells. *Science* 1999, 284:1168-1170.
8. Lagasse E., Connors H., A. I.-Dhalimy M., et al., Purified hematopoietic stem cells can differentiate into hepatocytes in vivo. *Nat Med* 2000, 6:1229-1234.
9. Theise N. D., Badve S., Saxena R., et al., Derivation of hepatocytes from bone marrow cells in mice after radiation-induced myeloblation. *Hepatology* 2000, 31:235-240.

10. Orlic D., Kajstura J., Chimenti S., et al., Transplanted hematopoietic stem cells repair myocardial infarcts [abstract]. *Blood* 2000, 96:221a.
11. Orlic D., Hematopoietic cells Regenerate Infarcted Myocardium. *Exp Hematol* 2001 (Suppl) 29:4.
12. Krause D. S., Theise N. D., Collector M., Henegariu O, Hwang S., Gardner R., Neutzel S., Sharkis S. J., Multi-organ, multi-lineage engraftment by a single bone marrow-derived stem. *Cell* 2001, 105:369-377.
13. Kawada, H. and Ogawa, M., Bone marrow origin of hematopoietic progenitors and stem cells in murine muscle. *Blood* 2001, 98:2008-2013.
14. Almeida-Porada G., Crapnell K., Porada C., et al., Transplantation of human neuronal stem cells into fetal sheep give rise to hematopoietic cells in vivo [abstract]. *Blood* 1999, 94:129a.

What is claimed is:

1. A composition of matter which comprises an anti-c-kit X anti-VCAM1 bispecific monoclonal antibody.

2. A kit comprising the composition of claim 1 and instructions for use.

* * * * *